United States Patent [19]

Bruso

[11] Patent Number: 4,692,307
[45] Date of Patent: * Sep. 8, 1987

[54] ADJUSTABLE TEST PACK

[75] Inventor: Loran H. Bruso, Ontario, Calif.

[73] Assignee: Warner-Lambert Company, Morris Plains, N.J.

[*] Notice: The portion of the term of this patent subsequent to Mar. 18, 2003 has been disclaimed.

[21] Appl. No.: 779,175

[22] Filed: Sep. 23, 1985

Related U.S. Application Data

[63] Continuation-in-part of Ser. No. 605,084, Apr. 30, 1984, Pat. No. 4,576,795, which is a continuation-in-part of Ser. No. 536,798, Sep. 28, 1983, Pat. No. 4,579,715.

[51] Int. Cl.4 .............................................. G01N 21/78
[52] U.S. Cl. ....................................... 422/58; 422/61; 436/1
[58] Field of Search ..................... 436/1; 422/55–57, 422/61, 86–88, 26

[56] References Cited

U.S. PATENT DOCUMENTS 4,478,792 10/1984 McConnaughey et al. .......... 422/56

Primary Examiner—Barry S. Richman
Assistant Examiner—C. M. Delahunty
Attorney, Agent, or Firm—Neil K. Nydegger

[57] ABSTRACT

An adjustable test pack for determining the efficiency of a vacuum in an autoclave comprises a porous bundle partially including open cell foam and having non-porous layers placed on its surface to leave a portion thereof exposed. A sheet with a steam sensitive indicator ink printed thereon is selectively embedded in the bundle for placement in an autoclave where a vacuum is drawn to evacuate air from the bundle through its exposed surface portions. Steam is then introduced to replace the evacuated air and react with the indicator ink wherever there is contact. The amount of indicator ink contacted by the steam may be varied according to the selected placement of the indicator sheet in the bundle and provides a measure of the efficiency of the vacuum.

5 Claims, 7 Drawing Figures

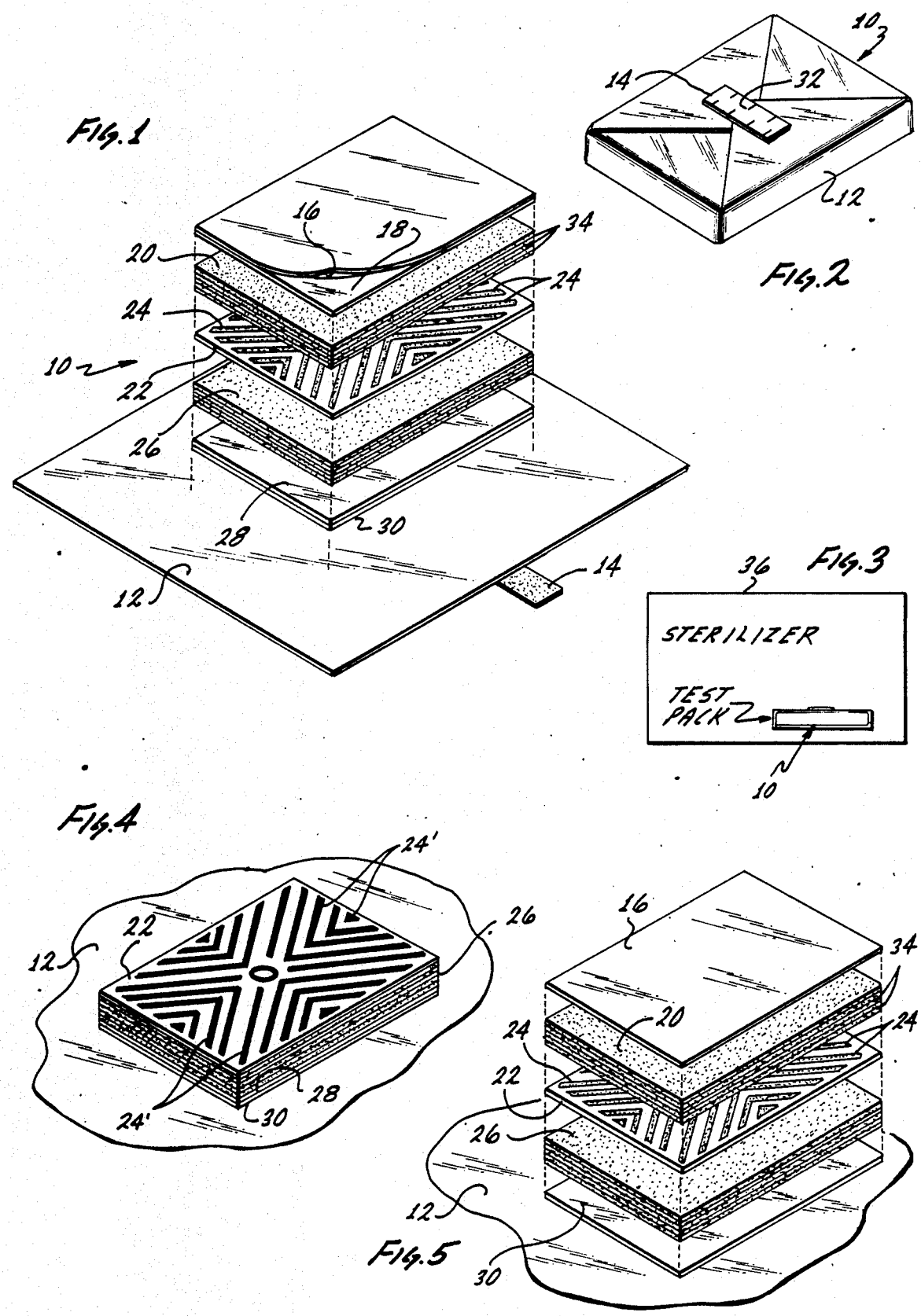

ADJUSTABLE TEST PACK

This application is a continuation-in-part of my prior application for an "mproved Disposable Sterilizer Vacuum Test Pack," Ser. No. 605,084, filed Apr. 30, 1984, now U.S. Pat. No. 4,576,795, which in turn is a continuation-in-part of an earlier application for a "Disposable Sterilizer Vacuum Test Pack," Ser. No. 536,798 filed Sept. 28, 1983, now U.S. Pat. No. 4,579,715.

BACKGROUND OF THE INVENTION

This invention relates generally to a device for testing the efficiency of a created vacuum. More specifically, the invention relates to an adjustable test pack which provides for the selective placement of an indicator sheet within the pack to determine the efficiency of the vacuum drawn in a steam sterilizing unit. The present invention is particularly, though not exclusively, useful in the testing of steam sterilizing equipment, such as an autoclave, used in the sterilization of hospital and medical equipment.

DESCRIPTION OF THE PRIOR ART

Well known in the pertinent art are several devices which indicate when sterilizing conditions have been achieved. Typically, such devices are indicator inks which are printed on a substrate and placed in the environment with the articles to be sterilized. Changes in the color of the inks show when effective sterilizing conditions have been achieved. Despite the efficacy of such indicators, they are effective only for the conditions to which they are exposed. Thus, unless the indicator can be placed directly into the particular area to be sterilized, there can be no real assurance that sterilizing conditions were achieved. This is a particularly troublesome problem where porous, permeable, holey or compartmentalized articles are concerned. Where such articles are concerned, there is a need to determine, with some degree of certainty, whether sterilizing conditions are achievable throughout the environment in which the articles are to be placed for sterilization. For example, in a hospital environment, it is frequently necessary to sterilize bundles, containers, packages or kits which have hard to reach areas where it is difficult or impossible to place a sterilization indicator. In such cases, there is a real need for assurance that the sterilizing medium has penetrated and been effective in these hard to reach areas.

When steam is used as the sterilizing medium, it has been the practice to place the articles in the chamber of an autoclave device. After a vacuum is drawn in the autoclave chamber, steam is introduced into the chamber as a sterilizing medium. In such devices it is particularly important that the efficiency of the vacuum system be determined because without an effective vacuum, air can remain entrapped in the hard to reach areas of articles and implements in the chamber. When steam is subsequently introduced into the chamber, the entrapped air forms bubbles which prevent the steam from being drawn into contact with those areas of the articles or implements where the air bubbles are located.

The industry standard for determining whether a particular autoclave system has been effective is the test commonly known as the Bowie-Dick test. In conducting this test, it has been the practice to wrap a steam sensitive indicator sheet in numerous towels and subject this package to the vacuum system and steam sterilizing cycle of the autoclave. This procedure is time consuming and laborious. Further, the efficiency of each test pack may vary depending on how carefully one adheres to the standard Bowie & Dick protocol.

In order to overcome the labor involved in constituting a pack of the type previously described and to provide more dependable and predictable reliability, it has been proposed that porous papers be used in lieu of towels. One example of such a device is presently being marketed by the Propper Manufacturing Company Inc. under the brand name Once-A-Day ®. Such a ready-made pack obviates the need for assembly and thereby reduces the amount of labor necessary to perform the test. Although such packs have less bulk than the aforementioned towel packs, there is still a need for an even smaller more compact test pack.

In addition to the need for a smaller test pack, there is the need for a test pack which affords a consistently high degree of assurance that sterilization conditions have been achieved This assurance can be enhanced by providing a pack which presents a more challenging and rigorous test for the vacuum system of an autoclave. When only porous materials are used to constitute the test pack, the pack's entire surface is exposed and a more rigorous test is obtained only by building up the porous layer which surrounds the steam sensitive indicator sheet. On the other hand, as envisioned by the present invention, nonporous layers are placed on the pack to reduce the surface area of exposed porous material. Such placement of nonporous layers establishes a more challenging test for the evacuation of air and introduction of steam by altering the gas permeable passageways of the test pack. As a consequence, this use of nonporous layers permits reduced dimensions for the test pack.

While the above cited advantages of using nonporous layers are significant for increasing the sensitivity of the test pack, it is still important that air and steam be able to circulate within the confined gas permeable passageways created in the test pack. Indeed, it is possible to make the test pack too sensitive. It will be understood, however, that the sensitivity of the test pack can be adjusted by either the selective placement of a nonporous layer or layers on the surface of the porous bundle or by increasing the porosity of materials within the bundle. In the present invention, a combination of these structural variations is used. There it is envisioned that a portion of the test pack is covered with a nonporous layer and the pack itself will include an open celled foam to control the degree of circulation of air and steam within the test pack. With this structure, a complete sterilization cycle forms an asymetrically shaped bubble within the pack which is forced against a nonporous layer. Also, in the present invention the selective positioning of the steam indicator sheet within the bundle permits a display of the test's results according to the desires of the operator.

Accordingly, it is an object of the present invention to provide an inexpensive, easily stored, small, cost effective test pack. It is yet another object of the present invention to provide a disposable adjustable test pack which is easily handled and which gives a reliable indication of the efficiency of the vacuum system. Still another object of the present invention is to provide an inexpensive test pack which is easily manufactured and does not take up excessive storage space. Still another object of the present invention is to provide a test pack which can be adjusted to display test results according to the desires of the operator.

SUMMARY OF THE INVENTION

A preferred embodiment of the novel adjustable test pack of the present invention includes a sheet having a steam discolorable indicator ink deposited thereon which is interposed between two porous pads of variable thickness. A foam layer is positioned against one of the porous pads to place this porous pad between the sheet and the foam layer. In this arrangement a bundle is formed wherein the foam layer defines the bottom of the bundle and the porous layer, which is not touching the foam layer, defines the top of the bundle. Disposed against both the top and the bottom of this porous bundle are nonporous layers which are preferably a plastic laminate. In this manner a test pack is formed that leaves portions of each porous pad and the foam layer exposed for evacuation of air therefrom and subsequent replacement with sterilizing steam. The extent to which steam penetrates the pack can be determined by subsequent inspection of the sheet. The resultant evidence of such exposure may then be used as a measure of the efficiency of the vacuum cycle of an autoclave. The entire pack can be covered with a CSR overwrap material and held together with a tape having an indicator ink imprinted thereon to show which packs have been subjected to a sterilization process.

The novel features of this invention, as well as the invention itself, both as to its structure and its operation will be best understood from the accompanying drawings, taken in conjunction with the accompanying description, in which similar reference characters refer to similar parts, and in which:

BRIEF DESCRIPTION OF THE DRAWINGS

FIG. 1 is an exploded perspective view of the contents of the adjustable test pack;

FIG. 2 is a perspective view of the adjustable test pack folded and ready for use in an autoclave device;

FIG. 3 is a schematic representation of the test pack in a sterilizer;

FIG. 4 is a perspective view of a portion of the test pack;

FIG. 5 is an exploded perspective view of an alternate embodiment of the test pack;

DESCRIPTION OF THE PREFERRED EMBODIMENT

Figure 6:
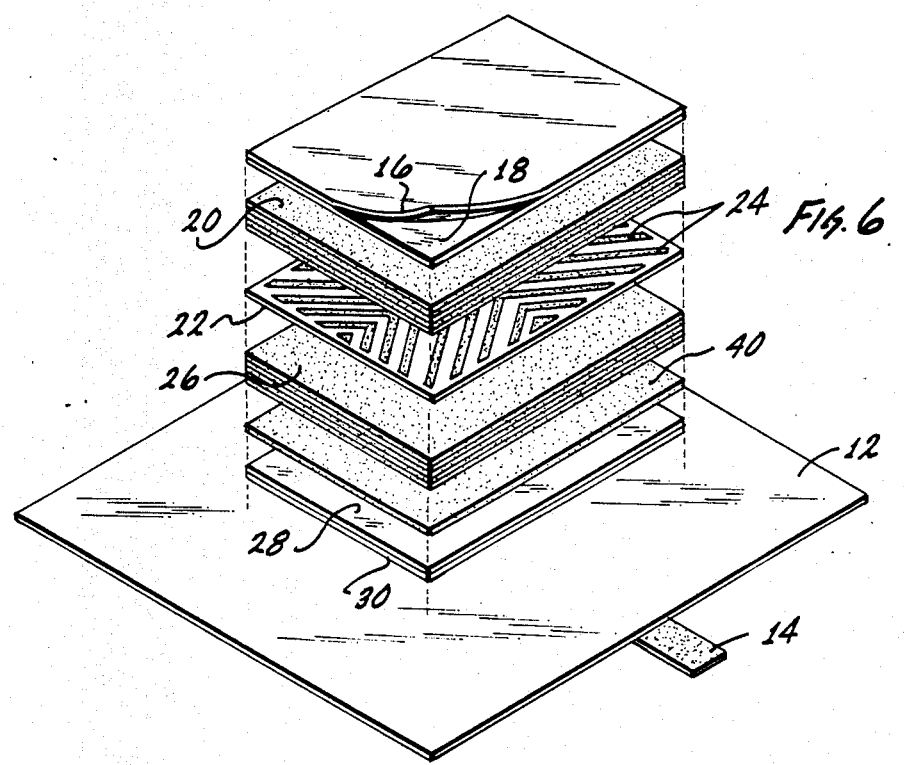
FIG. 6 is an exploded perspective view of the contents of the adjustable test pack incorporating a single foam layer.

Referring initially to FIG. 2, the adjustable test pack generally designated 10 is shown with the overwrap 12 in place and the autoclave indicator tape 14 securing the overwrap 12.

Disposed on the indicator tape 14 is a steam sensitive indicator ink 32 well known in the art which will indicate when the tape 14 and the adjustable test pack 10 have been exposed to a steam sterilization process.

In FIG. 6 the contents of the preferred embodiment of the adjustable test pack 10 are shown in an exploded perspective. Initially, it should be appreciated that an indicator sheet 22 is imprinted with an indicator ink 24 which will indicate the presence of a steam sterilization medium. As shown in FIGS. 1 and 6, the indicator ink 24 has not been exposed to a sterilization cycle. For comparison purposes, the indicator ink 24 on sheet 22 is shown in FIG. 4 as it would appear after exposure to a sterilization process. An indicator ink 24 such as the type described in the Berman patent, U.S. Pat. No. 2,118,144, which is discolorable in the presence of steam is preferable. For purposes of this invention, any porous material well known in the art, such as a blotter paper, on which ink can be deposited, may be used for the indicator sheet 22.

As shown in FIG. 6, the indicator sheet 22 is placed with a porous pad 20 disposed on one side of the indicator sheet 22 and a porous pad 26 disposed on the opposite side of the indicator sheet 22. Both porous pad 20 and porous pad 26 can be made from any porous material well known in the art. Further, the porous pads 20 and 26 can comprise a combination of various materials of differing porosity. In the preferred embodiment, porous pads 20 and 26 are formed as a stack of five 0.02" thick blotter papers of which blotter paper 34 is representative. It should be emphasized, however, that more or fewer blotter papers 34 of varying thicknesses can be used depending upon the particular needs of the device. Also, the dimensions of the pack 10 can be varied according to the number and thicknesses of blotter papers 34 needed to achieve a desired porosity value. Further, the indicator sheet 22 can be selectively positioned between any of the papers 34 to vary the distance of indicator sheet 22 from the geometrical center of test pack 10. Thus, the number of papers 34 comprising porous pad 20 may differ from the number of papers 34 comprising porous pad 26.

In the preferred embodiment shown in FIG. 6, a foam layer 40 is placed in position to cover the side of porous pad 26 that is opposite from the indicator sheet 22. Foam layer 40 can be made of any open cell reticulated foam that can withstand steam sterilization. For purposes of the present invention, either an open cell polyester foam or an open cell polyurethane foam are suitable for foam layer 40. However, as will be appreciated by those skilled in the art, any open cell reticulated foam which permits circulation of air and steam over the surface of porous pad 26 will suffice.

A substrate 18 having a nonporous layer 16 attached thereto by any means well known in the art, such as by lamination, is placed so the porous pad 20 is interposed between the nonporous layer 16 and the indicator sheet 22. A substrate 28 having a nonporous layer 30 attached thereto by any means well known in the art is placed so the porous pad 26 and foam layer 40 are interposed between the nonporous layer 30 and the indicator sheet 22. Preferably, both the nonporous layer 16 and nonporous layer 30 are a plastic. As indicated in FIGS. 1 and 6, nonporous layers 16 and 30 are plastic laminates. It should be appreciated, however, that any kind of material will be sufficient as the nonporous material for purposes of the invention as long as it is relatively nonporous and gas impermeable compared to the porous pads. For example, a metal sheet or foil or a layer of index cards could be effective for purposes of nonporous layer 16 and nonporous layer 30. Such a configuration is shown as an alternate embodiment in FIG. 5. As can be seen in FIGS. 1, 5 and 6, when all layers are placed in contact with each other, the edge portions of porous pad 20, porous pad 26 and foam layer 40 are left exposed to allow for evacuation of air from around indicator sheet 22 in a partial vacuum. Also, if desired, nonporous material (not shown) can be placed over parts of the edge portions of porous pads 20 and 26 to further reduce the amount of exposed surface.

The exposed surfaces on porous pad 20 and porous pad 26, i.e., those surfaces not covered by nonporous layer 16 or nonporous layer 30, permit the evacuation of air from and the subsequent introduction of steam into the pack 10. The steam, as is known in the relevant art, sensitizes the indicator ink 24 imprinted on indicator sheet 22 for the purpose of showing the effectiveness of the vacuum. It should be recognized that in the preferred embodiment the nonporous layers 16 and 30 block the passage of air and steam through the top and bottom surfaces of the pack 10 and redirect these gases through the edges of the porous pads 20 and 26. Thus, by using nonporous layers to confine gas movement into and out of the pack 10, the porous pads 20 and 26 can be reduced in size and still provide for an efficacious test of the partial vacuum. This, consequently, allows for a much more compact test pack 10.

As can be appreciated by cross referencing FIG. 1 and FIG. 2, the combination of indicator sheet 22, porous pad 20, porous pad 26, foam layer 40, nonporous layer 16 and nonporous layer 30 are stacked together and enclosed within a CSR overwrap 12. An autoclave indicator tape 14 can then be used to secure the overwrap 12. Use of an indicator tape 14 imprinted with a steam sensitive indicator ink 32, of a kind well known in the art, has the additional advantage of showing when the entire test pack 10 has been exposed to a steam sterilization process.

To assemble the pack 10, the indicator sheet 22 is placed between a porous pad 20 and a porous pad 26. Recall that porous pad 20 and porous pad 26 may differ in thickness according to the number of papers 34 used to constitute the respective pads. A foam layer 40 is placed on the side of porous pad 26 opposite indicator sheet 22. This combination of pads and foam layer is then interposed between a nonporous layer 16 and a nonporous layer 30. The entire combination is wrapped within a CSR overoverwrap 12 which is held in place by the autoclave indicator tape 14 to form the test pack 10.

Figure 7:
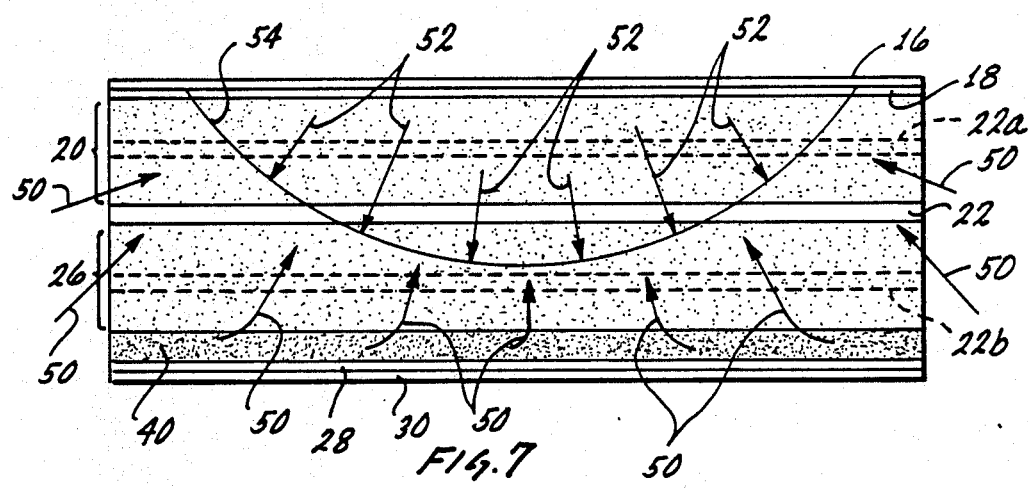
FIG. 7 is a cross-sectional schematic view in elevation of the test pack shown in FIG. 6 with representative air-steam dynamics.

The efficiency of an autoclave vacuum system is tested by placing the pack 10 into the coolest area of an autoclave chamber as shown schematically in FIG. 3. Generally, the coolest area is in the front of the autoclave chamber 36 on its floor near the door (not shown). Though there are several acceptable procedures, in a typical test procedure the pack 10 is first placed in this location in the autoclave chamber 36 and a vacuum is then drawn. Steam is then admitted into the autoclave chamber 36 for approximately 3½ minutes. If the vacuum has been ineffective, introduction of the steam will cause any air entrapped within the pack 10 to form as a bubble 54. As seen in FIG. 7 and subsequently discussed in greater detail, the presence of this bubble 54 stops further penetration of the steam and thus insulates whatever is within the bubble 54 from the sterilizing effect of the steam. The bubble 54 also prevents the steam from interacting with the indicator ink 24 in the vicinity of the bubble 54. After the sterilization cycle is complete, the adjustable test pack 10 is withdrawn from the autoclave chamber 36 and the indicator sheet 22 is examined to determine whether the indicator ink 24 has changed color and if so, to what extent it has changed color. Any failure of the indicator ink 24 to change color indicates the presence of air within the test pack 10 which was not evacuated during the drawing of the vacuum. Depending on the amount of air, an inefficiency of the vacuum system may be indicated. It follows that an inefficient vacuum will not provide the proper conditions for an acceptable sterili-zation process.

In addition to inefficiency of the vacuum system on the autoclave, there are other types of failures which will cause the indicator ink 24 to make an incomplete or only partial color change. For example, a timing error in the duration of the test, insufficient steam temperature, and incomplete injection of steam into the autoclave chamber 36 are all factors which could result in only a partial color change for indicator ink 24. However, unlike vacuum inefficiency, such failures generally show a uniform color change of indicator ink 24. As described above, vacuum inefficiency manifests itself as a discontinuity in color of the indicator ink 24 caused by the presence of an air bubble.

As will be discussed below, the pack 10 of the present invention functions to form an asymetrical air bubble 54 within the test pack 10. Further, the indicator sheet 22 can be positioned within the pack 10 to obtain a display on indicator sheet 22 which is familiar to the operator.

In FIG. 7 the air-steam dynamics of the test pack 10 are shown for the pack 10 which includes foam layer 40 and the nonporous layers 16 and 30 which are respectively placed against the top and bottom surfaces of test pack 10. After the test pack 10 has been subjected to a vacuum in the autoclave, steam represented by the arrows 50 enters test pack 10 and is opposed by any air remaining in the pack. The dynamics of the remaining air are shown by the arrows 52. Specifically, the steam 50 will enter the pack 10 until it reaches an equilibrium position with respect to the air 52 that was not evacuated from pack 10 during the drawing of the vacuum. Since foam layer 40 allows for relatively easy circulation of air and steam into and out of the pack 10, when steam 50 enters porous pad 26 it can do so in the manner shown in FIG. 7. The paths for steam 50 to enter porous pad 26 should be compared with those paths available into porous pad 20. As will be appreciated by the skilled artisan, the nonporous gas impermeable layer 16 blocks the passage of steam 50 into the pack 10 and thus directs steam 50 into pack 10 through the edges of porous pad 20 as shown in FIG. 7. Importantly, nonporous layer 16 not only redirects steam 50 entering the pack 10, it also blocks the escape of air 52 from pack 10. Consequently, as steam 50 enters the pack 10, the resultant bubble, which is indicated by line 54 in FIG. 7, is asymetrically formed within pack 10. More specifically, the bubble 54 formed within pack 10 is pressed against nonporous layer 16 and assumes a dome-shaped configuration having its base against the nonporous layer 16.

In light of the above, it can be appreciated that the extent of interaction between the steam and the indicator sheet will vary depending upon the location of indicator sheet 22 within pack 10. Adjustments in the location of sheet 22 within pack 10 can be accomplished by altering the size of porous pad 20 such as by varying the number of layers or papers 34 that constitute porous pad 20 or by varying the size of the layers or papers 34. It will be appreciated by the skilled artisan that the size of porous pad 26 can be altered in a similar manner. Insofar as results are concerned and still referring to FIG. 7, locating indicator sheet 22 in the position indicated by the character 22a will cause a smaller area of indicator sheet 22 to be affected by the steam penetration into pack 10. On the other hand, locating indicator sheet 22 in the position indicated by 22b will cause a larger area of indicator sheet 22 to be affected by steam penetration and may, in fact, cause all of the ink on indicator sheet to be affected by the steam which enters into the pack 10. Thus, it is possible for the operator in constructing the particular test pack 10 to selectively position indicator sheet 22 between or within the porous pads 26 and 20 to obtain a display on indicator sheet 22 according to the particular desires of the operator. This is particularly important during manufacture of the test pack 10 for at least two reasons. Firstly, the indicator sheet 22 can be placed within the porous papers 34 of the test pack 10 to obtain a display on indicator sheet 22 which is proportional to the display achieved by the towel pack of the standard Bowie & Dick test under similar conditions. Secondly, selective positioning of the indicator sheet 22 can compensate for differences in porosity of the materials used for porous pads 20 and 26.

It should also be understood that a plurality of indicator sheets 22 can be placed between the various papers 34 in pack 10. Such placement will depend only on the number of papers 34 in pack 10 and the desires of the operator. For example, it would be possible to simultaneously place indicator sheets 22 within pack 10 as shown by the characters 22, 22a and 22b in FIGS. 8 and 9. With such an arrangement, the profile of bubble 54 can be determined. Further, depending on the accuracy of profile that is desired, even more indicator sheets 22 could be used.

While the particular test pack as herein shown and disclosed in detail is fully capable of obtaining the objects and providing the advantages herein before stated, it is to be understood that it is merely illustrative of the presently preferred embodiment of the invention and that no limitations are intended to the details of construction or design herein shown other than as defined in the appended claims.

I claim:

1. A disposable pack for testing the efficiency of a steam sterilizer apparatus to create a vacuum which comprises:
    a porous bundle comprising a plurality of selectively porous layers wherein said bundle has a top surface and a bottom surface with an edge therebetween;
    a first nonporous gas impermeable layer positioned against said top surface of said bundle to block the passage of gas therethrough;
    a porous sheet with a steam sensitive indicator ink printed thereon positioned between layers of said bundle to indicate the efficiency of a sterilizer;
    a foam layer positioned against said bottom surface of said bundle having an edge substantially aligned with the edge of said bundle to permit circulation of gas over said bottom surface;
    a second nonporous gas impermeable layer positioned against said foam layer opposite said bundle to direct the passage of air through the edge of said foam layer; and
    a porous overwrap folded around said bundle, said sheet, said foam layer, said first nonporous gas impermeable layer, and said second nonporous gas impermeable layer to maintain the integrity thereof.

2. A disposable pack as cited in claim 1 further comprising a tape for holding said overwrap in place and having an indicator ink printed thereon to show when said pack has been exposed to a steam sterilizing medium.

3. A disposable pack as cited in claim 1 further comprising a plurality of said porous sheets with steam sensitive inks printed thereon which are selectively positioned between different layers of said porous bundle.

4. A disposable test pack for testing the efficiency of a steam sterilizer apparatus to create a vacuum which comprises:
    a first porous pad, a second porous pad and a porous sheet with a steam sensitive indicator ink printed thereon positioned between and stacked with said first and said second porous pads to form a bundle wherein said first porous pad defines a top surface, said second porous pad defines a bottom surface and an edge is established between said top surface and said bottom surface;
    a first nonporous gas impermeable layer positioned against the top surface of said bundle to block the escape of gas from said bundle as steam enters the bundle during operation of a sterilizer apparatus and to establish the amount of exposure of steam to said indicator ink on said sheet as an indication of the efficiency of the sterilizer;
    a foam layer positioned against said bottom surface of said bundle having an edge substantially aligned with the edge of said bundle to permit circulation of gas over said bottom surface;
    a second nonporous gas impermeable layer positioned against said foam layer opposite said bundle to direct the passage of air through the edge of said foam layer; and
    a porous overwrap folded around said bundle, said nonporous gas impermeable layer, said foam layer, and said second nonporous gas impermeable layer to maintain the integrity thereof.

5. A disposable pack as cited in claim 4 further comprising a tape for holding said overwrap in place and having an indicator ink printed thereon to show when said pack has been exposed to a steam sterilizing medium.

* * * * *